United States Patent [19]
Takahashi et al.

[11] 4,059,692
[45] Nov. 22, 1977

[54] TREATING IMPAIRED CONSCIOUSNESS WITH GLUTAMYL-L-HISTIDYL-L-PROLINAMIDE

[75] Inventors: Yoshinao Takahashi, Kobe; Kazuo Takeuchi, Tokyo, both of Japan

[73] Assignee: Takeda Chemical Industries, Ltd., Osaka, Japan

[21] Appl. No.: 669,455

[22] Filed: Mar. 22, 1976

[30] Foreign Application Priority Data

Apr. 3, 1975 United Kingdom ............... 13652/75
Nov. 26, 1975 United Kingdom ............... 48557/75

[51] Int. Cl.$^2$ ............................................. A61K 37/00
[52] U.S. Cl. .................................................. 424/177
[58] Field of Search .......................................... 424/177

[56] References Cited
U.S. PATENT DOCUMENTS 3,860,570  1/1975  Thomas et al. ...................... 424/177

*Primary Examiner*—Frederick E. Waddell
*Attorney, Agent, or Firm*—Wenderoth, Lind & Ponack

[57] ABSTRACT

The impaired consciousness due to functional or organic damage of the brain in human patients can be significantly improved and restored, without any undesirable side-effect, by administering to the patients L-pyroglutamyl-L-histidyl-L-prolinamide or its physiologically acceptable salts.

5 Claims, No Drawings

TREATING IMPAIRED CONSCIOUSNESS WITH GLUTAMYL-L-HISTIDYL-L-PROLINAMIDE

The present invention relates to a therapeutic means for improving and restoring impaired consciousness.

Recent progress and knowledge in diagnostic and therapeutic means of the neurosurgical field by ultrasonic and angiographic approaches and microsurgery have improved markedly the life-saving rate of the patients with impaired consciousness due to functional or organic damage of the brain such as cranial trauma, cerebrovascular disorder and brain tumor. However, even though these patients are prevented from dying, severely impaired consciousness often remains for a long time-period at a relatively high rate, and therefore, often causes the occurrence of the various complications such as respiratory or urinary tract infection, which are sometimes fatal to the patients. Although earlier recovery of the consciousness in these patients is essentially required for successful treatment, this requirement has not been fully satisfied up-to-date even by the present advanced medical care.

A series of efforts by the present inventors to establish the therapeutic means for improving the imparied consciousness in these patients resulted in introduction of L-pyroglutamyl-L-histidyl-L-prolinamide (thyrotropin releasing hormone; hereinafter briefly referred to as TRH) and its physiologically acceptable salts, the administration of which was unexpectedly found to significantly improve impaired consciousness.

Thus, the principal object of the present invention is to provide a method for the treatment of a human patient with impaired consciousness due to functional or organic damage of the brain, which comprises administering to the patient TRH or its physiologically acceptable salts. Another object of the present invention is to provide a pharmaceutical composition comprising TRH or its physiologically acceptable salts, which are usable in the abovementioned method. Other objects will be made clear from the description and claims hereinafter.

The method of the present invention is applicable to human patients with impaired consciousness due to functional or organic damage to the brain, such as cranial trauma, brain surgery, cerebrovascular disorder, brain tumors and the like. In particular, the method of the present invention is highly effective in patients with acute or subacute impairment of consciousness.

According to the present invention, TRH may be employed as the free base or in the form of a physiologically acceptable salt such as an acid addition salt e.g. a mineral acid salt (hydrochloride, sulphate, etc.) or an organic acid salt (acetate, tartrate, etc.). TRH tartrate is especially convenient for the administration. TRH or its salts are generally administered by the parenteral routes such as intravenous or intramuscular routes to the patients. The therapeutic dosage depends upon the route and upon the severity of impaired consciousness in each patient, and it may generally be chosen from within the range of from about 100 to about 5,000 $\mu$g. in terms of free TRH per adult human patient per day, more particularly from about 500 to about 5,000 $\mu$g. in terms of free TRH per adult human patient per day, when parenterally e.g. intravenously or intramuscularly administered. In case of those patients having swallowing capacity TRH or its salts may be orally administered. In this case, the dosage may be of course chosen from within the abovementioned range, but it may be increased over the said range, for example, up to about 150 mg. in terms of free TRH per adult human patient per day.

Pharmaceutical compositions containing TRH or its salts can be prepared by per se conventional techniques for the preparation of injections, powders, capsules, tablets, pills, and the like. For intravenous or intramuscular injections, an injectable solvent such as physiological saline is employed. When intravenous drip infusion is applied, an optional carrier such as an aqueous solution of glucose may be employed. If desired, the medicament of the present invention may be administered in combination with other drugs for impaired consciousness, such as cytidine -5'-diphosphate choline, mecrofenoxate, pyrithioxin and the like.

According to the present invention, the impaired consciousness due to functional or/and organic damage of the brain can be significantly improved and restored without any undesirable side-effect and therefore, the present invention highly contributes to the neurological and neurosurgical fields.

The following clinical data and Examples are merely for illustrative purposes and are not to be construed as limitations of the present invention.

Throughout the foregoing description as well as in the following clinical data, Examples and Claims, "$\mu$g.", "mg." and "ml" respectively refer to "microgram(s)", "milligram(s)" and "milliliter(s)".

CASE 1

Nine year old boy: Postoperative state of haematoma of right frontal lobe caused by cranial trauma.

Before administration, the patient was able to respond to only painful stimuli with a verbal expression of pain, otherwise being unconcious with a slight palpebral opening. Such conscious state lasted without modification for a further 10 days. The daily intramuscular injection of 292 $\mu$g. of TRH tartrate (dissolved in 0.8 ml of a sterile physiological saline; 200 $\mu$g. in terms of free TRH) successively for 10 days. On the 5th day of the treatment, there was produced a prompt verbal reply with a smile to the interview by the doctor. On the 7th day, he was able to ride and sit by himself on a wheelchair. The next day, he was able to go to a stool with support and he was able to sit by himself on the bed and to have a conversation with others on one day after the termination of the daily administration.

CASE 2

59 year old male: Postoperative state of metastatic brain tumor on right frontal and pariental lobes.

At the time of hospitalization the patient exhibited blood stagnation at the retinal papilla, functional impairments of right V, VI, VII, VIII, and X cerebral nerves, left motor and sensory hemiplegia. X-ray film of the thorax demonstrated a fist-sized tumor in the right inferior lobe of the lung and the scintigram of the brain demonstrated a positive figure at the right frontal and parietal lobes. Craniotomy performed for the reduction of the intracranial pressure was followed by the gradual deterioration of consciousness. Therefore, TRH tartrate in the daily dose of 730 $\mu$g. (dissolved in 20 ml of 20% glucose; 500 $\mu$g. in terms of free TRH) was administered by intravenous drip infusion of 13 days. On the 2nd day of the treatment, the significant improvement of the conscious state was accompanied with the improvement of orientation ability, which was previously impaired markedly. The significantly improved conscious state was found to persist for about one month after the termination of the TRH treatment but progression of the bodily emaciation associated with coma resulted in death four months after the operation.

CASE 3

Eight year old boy: Brain contusion due to cranial trauma.

The boy suffered from bodily contusion and loss of consciousness by collision on his bicycle with a train. At the time of hospitalization, the bilateral facilitation of the knee-jerk reflex was associated with the positive Babinski's reflex bilaterally. The daily administration of 730 μg. TRH tartrate (dissolved in 20 ml of 20% glucose; 500 μg. in terms of free TRH) by intravenous drip infusion successively for 10 days resulted in the sluggish appearance of Babinski's reflex on the 2nd day followed by the disappearance on the 3rd day. The impaired consciousness began to be improved from the 4th day and the impaired orientation was markedly improved. He was able to walk on one day after the termination of the daily administration, and recovered without any neurological abnormality.

CASE 4

Forty year old woman: Post-operative state of glioblastoma.

The surgical resection of glioblastoma by cranitomy was gradually followed by a worsening of the general condition associated with impaired consciousness for 3 months. The daily administration of 1,460 μg. of TRH tartrate (dissolved in 500 ml of electrolyte solution; 1,000 μg. in terms of free TRH) by intravenous drip infusion for 10 days prolonged the time-length of the palpebral opening from the 4th day to cause movement of both eyeballs in adaptation with the shift of the object, followed by a remarkable improvement of the consciousness.

CASE 5

53 year-old male: Traumatic protracted coma.

The patient had been thrown from a motor bike and disturbance of consciousness had become apparent immediately after the accident. There was movement of the extremities and grimacing of the face in response to pain stimulus. The disturbance of consciousness continued thereafter and the disturbance had become fixed for 2 years prior to medication with TRH. TRH tartrate in the daily dose of 7,300 μg. (dissolved in 200 ml of electrolyte solution; 5,000 μg. in terms of free TRH) was administered by intravenous drip infusion. Two days after start of the treatment, he began to respond with a sound to vocal questioning and turn the eyes towards the questioner. He also began to answer friends vocally with "Ah", "Ah". From about the fifth day, he began to respond vocally to calling, actively move his hands and eyes and turn his head towards his visitor; showing a definite improvement in the level of consciousness. The medication was terminated at the 10th day. No side effects were observed during the treatment period.

This case, which had not responded to any of the conventional forms of treatment, showed a significant improvement of impaired consciousness for the first time to treatment with 5,000 μg. (in terms of free TRH) per day of TRH.

CASE 6

60 year-old male: Aneurysm of left cerebral artery.

After an attack of subarachnoid hemorrhage, it was noted that he had lost accessibility with people around him and volition, and that he had been in an abstract state. This condition had lasted for 1 month. TRH tartrate in the daily dose of 3,650 μg. (dissolved in 200 ml of electrolyte solution; 2,500 μg. in terms of free TRH) was administered by intravenous drip infusion for 10 days. On the third day of the treatment, the abstract state disappeared and he nodded and smiled to other people's conversation. Accessibility with people around him improved and the state of consciousness was restored close to normal on the seventh day. No noteworthy side effects were observed.

CASE 7

43 year-old male: Sequelae of head trauma.

The patient fell from a road down into the river bed from a height of about 2.5 meters and hit the back of his head. Consciousness was lost for about 3 hours. He was immediately hospitalized and consciousness slowly improved for 13 months. Before administration of TRH the state of consciousness was such that he was able to answer questions promptly but agnosia and abnormal behavior were prominent. He often remained vacantly in bed the whole day and a depression of the level of consciousness was apparent.

TRH tartrate was orally administered in the daily dose of 8.76 mg. (6 mg. in terms of free TRH) for 2 weeks. From the third day of medication normalization of behavior and spontaneous activity such as sitting up in bed and reading a book or watching television became apparent.

After 1 week of medication he began to actively converse with people around him. This improvement in the level of consciousness was retained even after medication was terminated at 2 weeks. He was discharged after 3 weeks and has returned to his former work.

No side effects were noted during the period of medication.

CASE 8

50 year-old male: Sequelae of head trauma.

The patient had been in a traffic accident and had hit the right, front of the head severely. The skull had been fractured and consciousness had been lost for 35 days. The level of consciousness had gradually improved but 2 years later, he was only able to look after himself and agnosia, disorientation and loss of volition were present. Pneumoencephalogram revealed extensive atrophy of the brain. The electroencephalogram showed a trend for slow waves overall. From the findings, it was determined that this was a case of depression of the level of consciousness due to generalized damage of the brain due to cranial trauma.

TRH tartrate was given orally in the daily dose of 17.52 mg. (12 mg. in terms of free TRH), and after 2 weeks, he began to actively watch television or play the pinball machine, which he had enjoyed prior to the accident, though there was little change in the agnosia and disorientation. Conversation with other people also increased in frequency.

Medication was terminated after 2 weeks but there has been no marked change in the condition of the patient after 3 months. No side effects have been observed during and after termination of medication.

EXAMPLE 1

Tablets containing 2.928 mg. of TRH tartrate (2.000 mg. in terms of free TRH) and having the following composition are prepared by per se known techniques:

| | |
|---|---|
| TRH tartrate | 2.928 mg. |
| lactose | 65.072 mg. |
| corn starch | 39.800 mg. |
| hydroxypropylcellulose | 2.000 mg. |
| magnesium stearate | 0.200 mg. |
| | 110.000 mg. per tablet |

EXAMPLE 2

An injection for intramuscular use is prepared by dissolving 730 μg. of TRH tartrate (500 μg. in terms of free TRH) in 1 ml of a sterile physiological saline containing 5% of sorbitol.

EXAMPLE 3

An injection for intravenous drip infusion is prepared by dissolving 3,650 μg. of TRH tartrate (2,500 μg. in terms of free TRH) in 500 ml of an electrolyte solution.

What is claimed is:

1. A method for the treatment of a human patient with impaired consciousness due to cranial trauma, brain surgery, cerebrovascular disorder, or brain tumor, which comprises administering to such patient an effective amount of L-pyroglutamyl-L-histidyl-L-prolinamide or a physiologically acceptable salt thereof.

2. A method as claimed in claim 1, wherein L-pyroglutamyl-L-histidyl-L-prolinamide or a physiologically acceptable salt thereof is administered parenterally or orally.

3. A method as claimed in claim 2, wherein L-pyroglutamyl-L-histidyl-L-prolinamide or a physiologically acceptable salt thereof is administered intravenously or intramuscularly in an amount of from about 100 to about 5,000 μg. in terms of free L-pyroglutamyl-L-histidyl-L-prolinamide per adult patient per day.

4. A method as claimed in claim 2, wherein L-pyroglutamyl-L-histidyl-L-prolinamide or a physiologically acceptable salt thereof is administered orally in an amount of from about 100 μg. to about 150 mg. in terms of free L-pyroglutamyl-L-histidyl-L-prolinamide per adult patient per day.

5. A method as claimed in claim 1, wherein the physiologically acceptable salt is tartrate.

* * * * *